United States Patent [19]

Hon

[11] Patent Number: 4,476,871
[45] Date of Patent: Oct. 16, 1984

[54] MONITORING OF CERVICAL DILATATION DURING LABOR

[75] Inventor: Edward H. Hon, Bradbury, Calif.

[73] Assignee: American Home Products Corporation, New York, N.Y.

[21] Appl. No.: 371,371

[22] Filed: Apr. 23, 1982

[51] Int. Cl.³ .............................. A61B 5/04; A61B 5/10
[52] U.S. Cl. ..................................... 128/642; 128/696; 128/775; 128/778; 200/81.4; 200/83 N
[58] Field of Search ............... 128/774, 775, 778, 780, 128/748, 639, 642, 670, 695, 696, 698, 700; 200/83 N, 81.4; 73/716

[56] References Cited

U.S. PATENT DOCUMENTS

| | | | |
|---|---|---|---|
| 3,480,003 | 11/1969 | Crites | 128/780 |
| 4,073,287 | 2/1978 | Bradley | 128/642 |
| 4,168,703 | 9/1979 | Kenigsberg | 128/748 |
| 4,299,230 | 11/1981 | Kubota | 128/748 X |

FOREIGN PATENT DOCUMENTS 2453630 12/1980 France ........................... 128/642

OTHER PUBLICATIONS

Ulmsten et al., Electromedia, vol. 48, Jan. 1980, pp. 9–12.

Primary Examiner—Kyle L. Howell
Assistant Examiner—John C. Hanley
Attorney, Agent, or Firm—Edward M. Blocker

[57] ABSTRACT

A device for use in monitoring cervical dilatation during labor. The device comprises an elongated member having a longitudinal axis, the member being adapted to be positioned between a fetal presenting part and a cervix; and means for measuring the recession of the cervix with cervical dilatation from the elongated member and along the longitudinal axis thereof. Also provided are systems and methods of monitoring cervical dilatation during labor. An elongated member having a longitudinal axis is positioned between a fetal presenting part and a cervix. The elongated member is anchored against longitudinal movement with respect to a maternal reference point. The recession of the cervix with cervical dilatation from the elongated member and along the longitudinal axis is measured.

9 Claims, 15 Drawing Figures

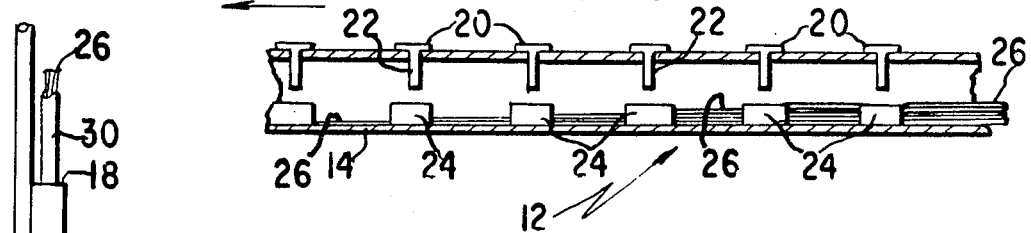
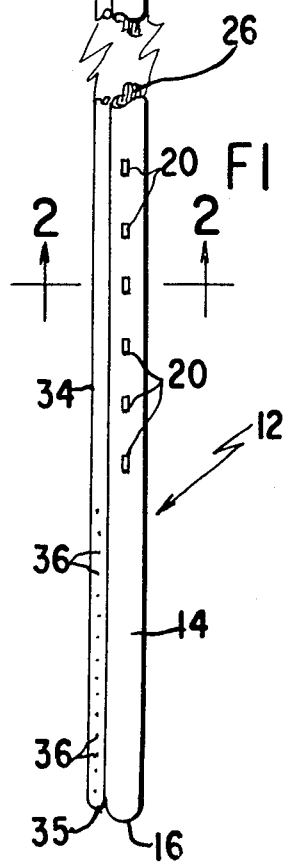
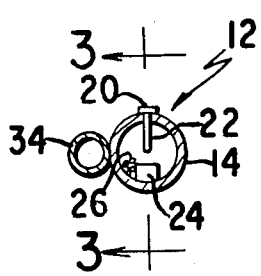
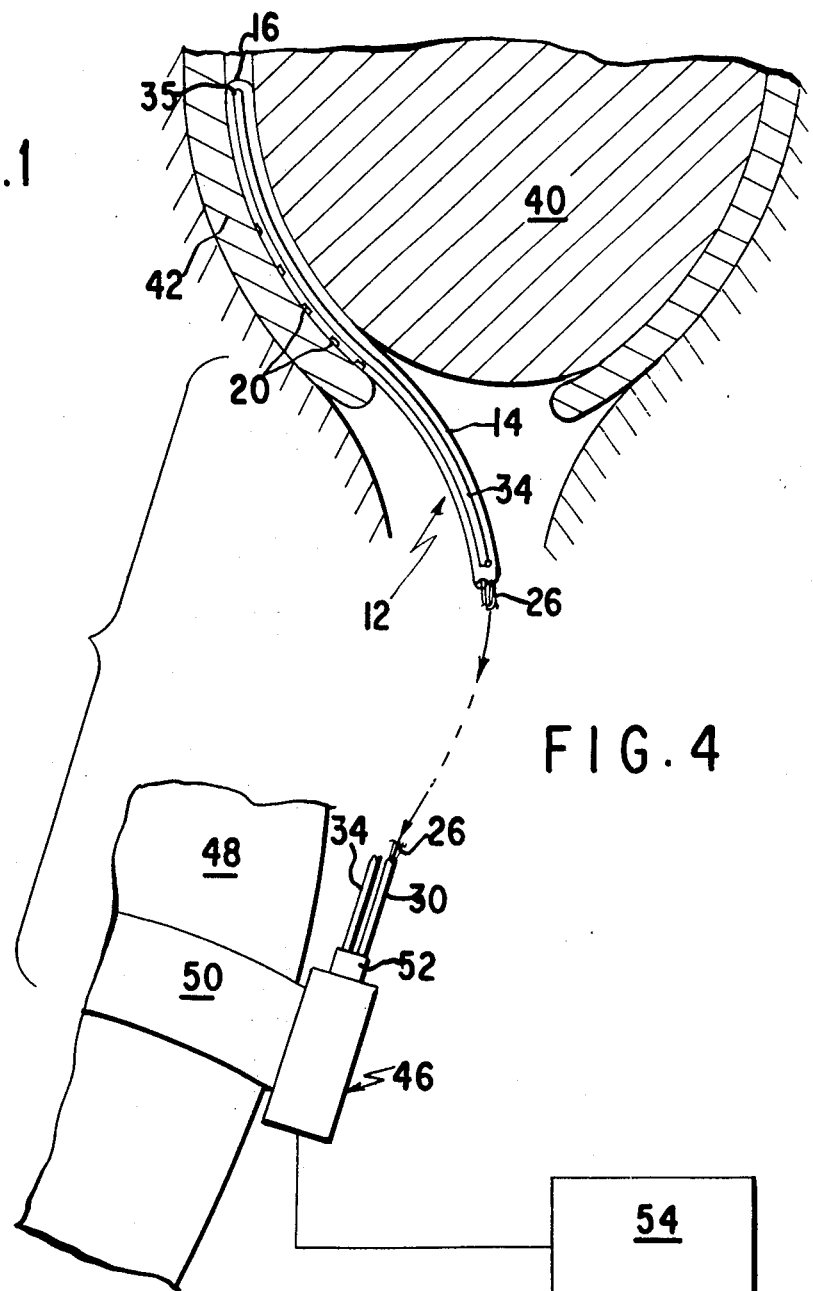

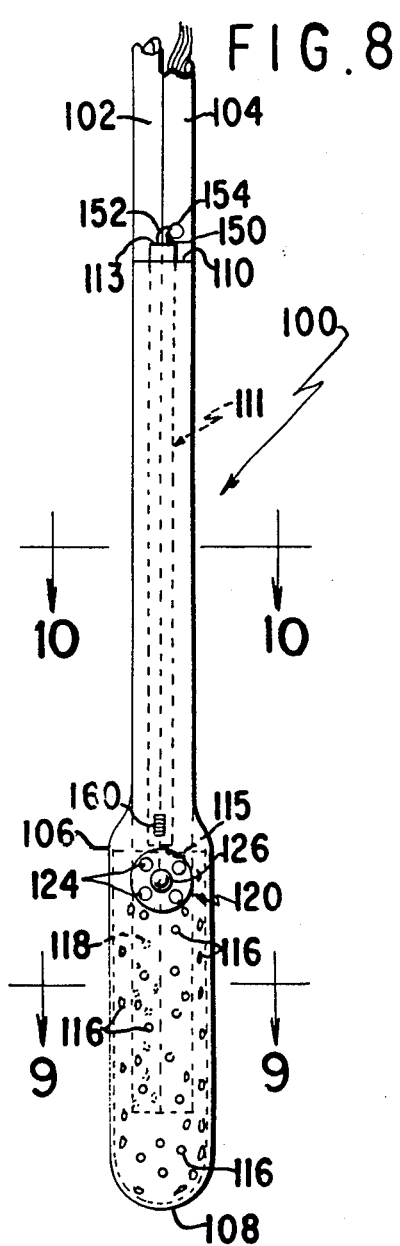
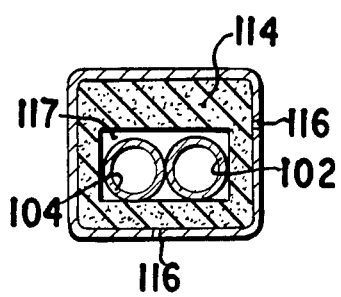
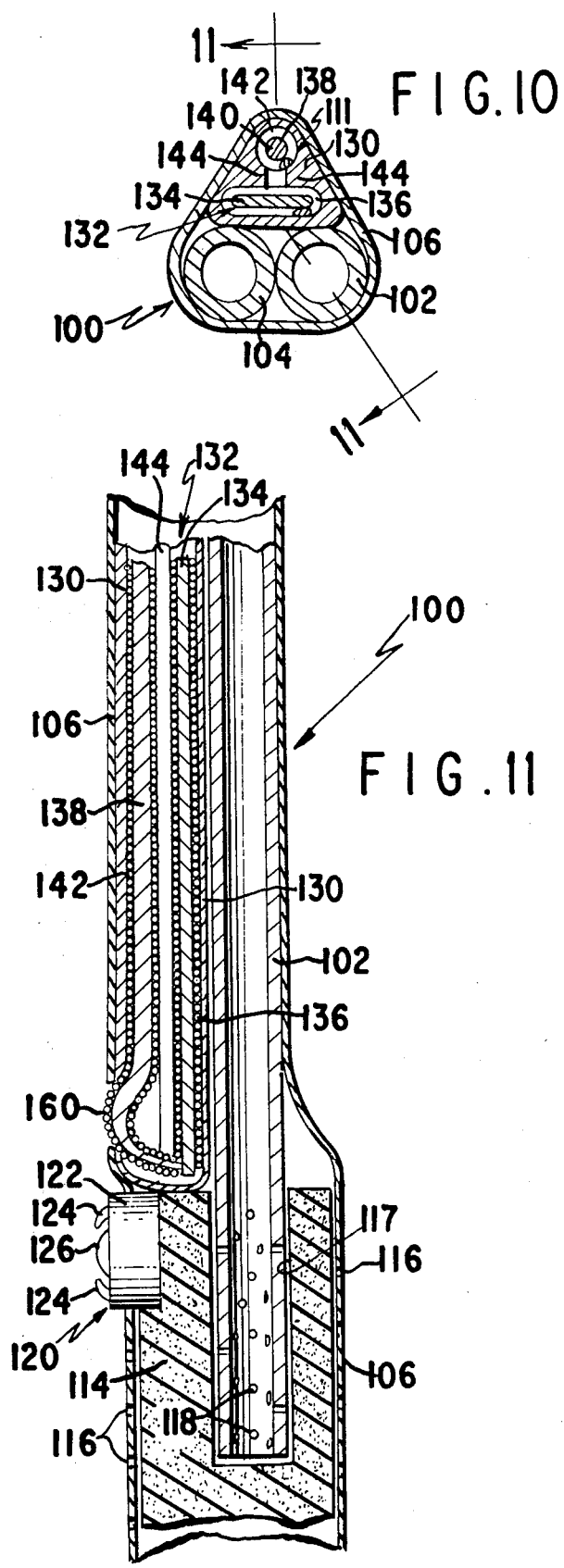

MONITORING OF CERVICAL DILATATION DURING LABOR

BACKGROUND OF THE INVENTION

The present invention relates to the monitoring of cervical dilatation during labor.

Traditionally cervical dilatation is estimated by the physician through a vaginal examination. Accordingly, this measurement cannot be made on a continuous basis and only provides a rough estimate of actual cervical dilatation.

While various devices have been devised to assist the physician in measuring cervical dilatation via a vaginal examination, they do not provide the capability of measuring cervical dilatation on a continuous basis over time.

Still other devices have attempted to provide a continuous dilatation monitoring capability. Such devices are constructed as calipers designed to attach to diametrically opposed surfaces of the external os of the cervix. As the cervix dilates, the degree of separation of the caliper arms is monitored to measure the dilatation. The ends of the caliper arms must however, be securely fixed to the external os, so that such devices typically provide needles or barbs which cut into the cervical tissues to prevent the caliper arms from being loosened from the cervix during labor. Obviously, such devices pose a substantial risk of injury to the cervical tissues. They are also relatively complex and difficult to use.

SUMMARY

It is, therefore, a general object of the present invention to provide devices, systems and methods for monitoring cervical dilatation during labor.

It is a further object of the present invention to provide such devices, systems and methods which are capable of monitoring cervical dilatation continuously over time.

It is an additional object of the present invention to provide such devices, systems and methods which do not pose a substantial risk of injury to the mother or the fetus.

It is still another object of the present invention to provide such devices which are relatively uncomplicated and inexpensive to manufacture, and easy to use.

In accordance with one aspect of the present invention, a device is provided for monitoring cervical dilatation during labor. The device comprises an elongated member having a longitudinal axis, the member being adapted to be positioned between a fetal presenting part and a cervix. Means are provided for measuring the recession of the cervix with cervical dilatation from the elongated member and along the longitudinal axis thereof. It is thus not necessary to affix the device to the cervical tissues, nor is it necessary to penetrate such tissues to monitor cervical dilatation, with the concomitant risk of injury. The device is relatively easy to use, as it is not necessary to affix it to the cervix.

In accordance with another aspect of the present invention, a system is provided for monitoring cervical dilatation during labor. The system comprises an elongated member having a longitudinal axis, the member being adapted to be positioned between a fetal presenting part and a cervix; means for anchoring the elongated member against longitudinal movement with respect to a maternal reference point; and means for measuring the recession of the cervix with cervical dilatation from the elongated member and along the longitudinal axis.

In accordance with still another aspect of the present invention, a method is provided for monitoring cervical dilatation during labor. The method comprises the steps of: positioning an elongated member having a longitudinal axis between a fetal presenting part and a cervix; and measuring the recession of the cervix with cervical dilatation from the elongated member and along the longitudinal axis. In a preferred embodiment, the method further comprises the step of anchoring the elongated member against longitudinal movement with respect to a maternal reference point.

In accordance with yet still another aspect of the present invention, a device for use in monitoring intrauterine pressure during labor is provided. The device comprises a tube having a proximal end adapted to be coupled to a pressure sensing device and a distal end having at least one aperture for admitting fluids into the lumen of the tube; and means for agitating fluids adjacent said at least one aperture for maintaining the patency of said at least one aperture during the monitoring of intrauterine pressure.

These and other aspects of the present invention will be more apparent from the following description of certain advantageous embodiments when considered together with the accompanying drawings.

BRIEF DESCRIPTION OF THE DRAWINGS

FIG. 1 is a plan view, partially cut-away, of a device for monitoring cervical dilatation during labor;

FIG. 2 is a cross-sectional view the device of FIG. 1 taken along the lines 2—2 in FIG. 1;

FIG. 3 is a partial, cross-sectional view of the device of FIG. 1 taken along the lines 3—3 in FIG. 2;

FIG. 4 is a partially cut away view of the device of FIG. 1 positioned between a fetal presenting part and a cervix (both shown in cross section) for monitoring cervical dilatation during labor, the device being anchored against longitudinal movement by means of fixation to a device secured to a maternal leg;

FIG. 8 is a plan view of a distal portion of a device in accordance with the present invention for use in monitoring several different physiological parameters during labor;

FIG. 9 is a cross sectional view of the device of FIG. 8, taken along the lines 9—9 thereof;

FIG. 10 is a cross sectional view taken along the lines 10—10 in FIG. 8;

FIG. 11 is a partially broken away, partially cross sectional view taken along the lines 11—11 in FIG. 10;

DETAILED DESCRIPTION OF CERTAIN PREFERRED EMBODIMENTS

Figure 5:
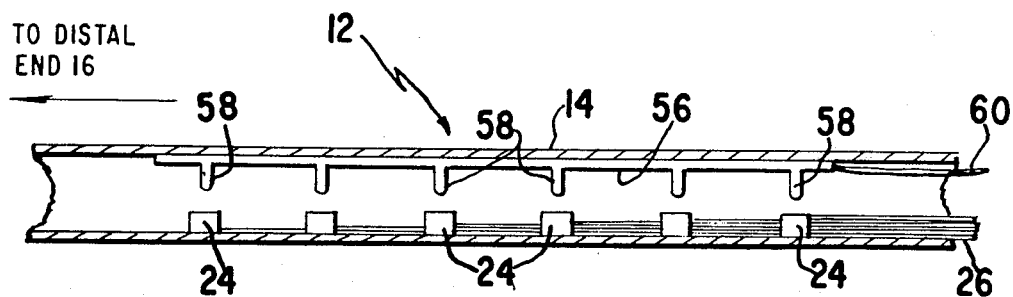
FIGS. 5, 6 and 7 are cross-sectional views, partially cut away, of further embodiments of the present invention.

With reference first to FIGS. 1, 2 and 3, a device 12 is shown for monitoring cervical dilatation during labor. The device 12 includes an elongated member in the form of a compressible tube 14 having a sealed distal end 16 and a proximal end 18. A plurality of ECG electrodes 20 are spaced axially along the outer wall of tube 14. Electrodes 20 preferably are spaced at regular intervals of one centimeter measured axially and are radially aligned with respect to the tube 14. Each of the electrodes 20 includes a projection 22 extending radially inwardly of tube 14 to serve as a switch contact for coupling the electrode to a monitoring device when the tube 14 is compressed at the location of the respective electrode 20. A plurality of contact pads 24 are provided, each being affixed to the inner wall of tube 14 and aligned axially with a respective electrode 20 and radially opposed to its respective projection 22, such that the compression of the tube 14 at the location of a given electrode 20 will bring its projection 22 in contact with its respective contact pad 24. Accordingly, each projection 22 and its corresponding contact pad 24 together comprise a normally open switch which is operative to be closed in response to pressure exerted thereat. Each of contact pads 24 has a respective conductor 26 connected at a first end to the contact pad 24 and extending axially within the lumen of the tube 14 toward the proximal end thereof. A second, relatively more rigid tube 30 is coupled with tube 14 at the proximal end thereof and serves as a conduit for conductors 26 for directing the conductors to means for detecting the maternal ECG, whereby the contact pads 24 are adapted to be coupled to such ECG detecting means.

The device of FIGS. 1 through 3 also includes a third tube 34 affixed in side by side relationship with tube 14. The tube 34 has a sealed distal end 35 and a multiplicity of pin holes 36 adjacent distal end 35. The third tube 34 is adapted for measuring pressure in the lower uterine segment during labor by transmitting the pressure therein through a column of fluid in the tube 34 to a pressure measuring device at the proximal end of tube 34. Tube 34 is also displaced radially approximately 90 degrees to the electrodes 20.

With reference to FIG. 4, the device 12 is shown in position between a fetal presenting part 40 and the cervical wall 42 of a woman in labor, after the cervix has begun to dilate and the membranes have broken. The doctor has aligned the device 12 such that the electrodes 20 face the cervical wall. The tube 14 is prevented from rotating which would turn the electrodes 20 away from the cervical wall, by virtue of the presence of tube 34 in side by side relationship with tube 14. Accordingly, tube 34 serves to radially position the electrodes 20 in contact with the cervix.

Also shown in FIG. 4 is an anchoring means in the form of a leg plate 46 affixed to a maternal leg 48 by means of a strap 50. The leg plate 46 has a terminal 52 to which the tubes 30 and 34 are affixed after the device 12 has been positioned between the cervix 42 and fetal presenting part 40. Terminal 52 provides a means for measuring the pressure of the fluid in tube 34, for example, a strain gauge. Terminal 52 also serves to couple the conductors 26 to ECG detection circuitry, shown schematically as 54. By virtue of its attachment to leg plate 46, the device 12 is anchored against longitudinal movement with respect to the maternal leg. Accordingly, as the cervical wall 42 recedes from the fetal presenting part 40 as labor progresses, the cervical wall will likewise recede axially of tube 14 toward the distal end 16 thereof. By virtue of their contact with the cervical wall, the electrodes 20 detect the maternal ECG therefrom. As the cervix recedes with cervical dilatation, therefore, those of the electrodes 20 which are closest to the proximal end of the tube 14 will first break contact with the cervix. Moreover, since the fetal presenting part 40 and the cervix 42 are not compressing the tube 14 at the axial locations of such electrodes 20, the conductors 26 coupled with the contact pads 24 corresponding to such conductors 20 will fail to provide the maternal ECG. The remaining electrodes 20 will be coupled to their contact pads 24 and thus to the respective conductors 26 by virtue of the compression of the tube 14 thereat between the fetal presenting part 40 and the cervical wall 42, thus to provide the maternal ECG on such conductors 26. As the cervix recedes further toward the distal end 16 of tube 14 with cervical dilatation, successively more of the electrodes 20 and their respective contact pads 24 will break contact thus opening the circuits to their respective conductors 26. The device 12, therefore, provides a means for measuring the recession of the cervix with cervical dilatation from the tube 14 and along the axial dimension thereof through the detection of those positions along the axis of tube 14 at which pressure is exerted thereon by the fetal presenting part and the cervix.

FIG. 5 is a cross-sectional view, partially cut-away, of a further embodiment of the present invention wherein elements corresponding to those shown in FIGS. 1 through 4 are designated by the same reference numerals. In the device of FIG. 5, the electrodes 20 are replaced by a conductive strip 56 affixed to the inner wall of the tube 14 and extending axially thereof in opposed radial position with the contact pads 24. Conductive strip 56 has a plurality of projections 58 integral therewith radially aligned with one another, each projection being directed toward a respective contact pad 24. An additional conductor 60 is connected at a first end to strip 56 and extends axially to the proximal end of tube 30 together with conductors 26. A second end of conductor 60 is adapted to be coupled to the terminal 52. In the embodiment of FIG. 5, the tube 34 is aligned with tube 14 in the same manner as shown in FIG. 1 and is radially displaced from the pads 24 and the strip 56 by approximately 90 degrees. Accordingly, when the FIG. 5 embodiment is positioned between the fetal presenting part and the cervix in the manner shown in FIG. 4, the projections 58 and the pads 24 are each aligned with a respective one of the fetal presenting part 40 and the cervical wall 42. It will be appreciated that as the tube 14 is compressed between the fetal presenting part 40 and the cervical wall 42 at various locations along the conductive strip 56, certain ones of the projections 58 will be forced into contact with their respective contact pads 24, thus completing a circuit between the additional conductor 60 and the respective conductors 26 connected to those contact pads 24 in contact with projections 58. Accordingly, by monitoring the continuity between the conductor 60 and the respective ones of the conductors 26, the recession of the cervix along the tube 14 may be monitored continuously over time.

Figure 6:
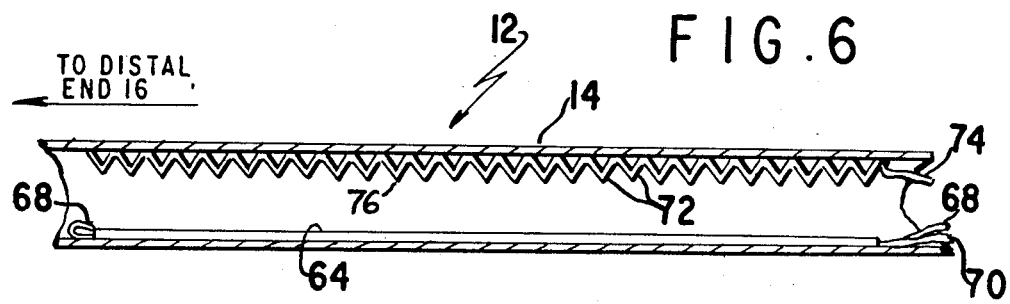

FIG. 6 is a cross-sectional view, partially broken away, of still another embodiment of the present invention. In FIG. 6, elements corresponding to those in the preceding figures are designated by the same reference numerals. In the FIG. 6 embodiment, an elongated resistive element 64 is disposed on the inner wall of tube 14 to extend axially there along. A first conductor 68 is connected to a distal end of element 64 and extends axially within tube 14 towards the proximal end thereof and therefrom through tube 30 for coupling to monitoring means. A second conductor 70 is connected to the proximal end of resistive element 64 and extends axially with first conductor 68 through tube 14 and tube 30 for coupling to monitoring means. A corregated conductive strip 72 is also mounted on the inside wall of the tube 14 in opposed radial relationship with the resistive element 64, providing a plurality of regularly spaced projections 76 facing inwardly toward resistive element 64. A third conductor 74 is connected to the proximal end of conductive strip 72 and extends axially of tube 14 with conductor 68 and 70 through tube 30 for coupling to monitoring means. It will be appreciated that the embodiment of FIG. 6 provides a means for detecting the locations along the axial extent of tube 14 at which the tube has been compressed, since the resistance, for example, between conductor 70 and conductor 74 will vary linearly with the distance between the proximal end of element 64 and the closest point at which the resistive element 64 and the projections 76 come in contact. The tube 34 is displaced radially from the resistive element 64 and the conductive strip 72 by 90 degrees such that, in the same manner as described in connection with the preceding figures, one of the resistive element 64 and the conductive strip 72 is radially aligned with the cervical wall and the other is aligned with the fetal presenting part, to ensure the proper operation of the device.

The resistive element 64 may be constructed in a variety of ways. In accordance with one advantageous construction thereof, the element 64 includes a flexible, elongated plastic base. A silicone adhesive is placed on a surface of the plastic base and graphite particles are deposited on the layer of adhesive. Then the assembly is subjected to pressure and heating to cause the particles to adhere to the plastic base. In accordance with a further embodiment of the resistive element 64, a similar flexible, elongated plastic base has a resistive wire wound thereabout.

Figure 7:
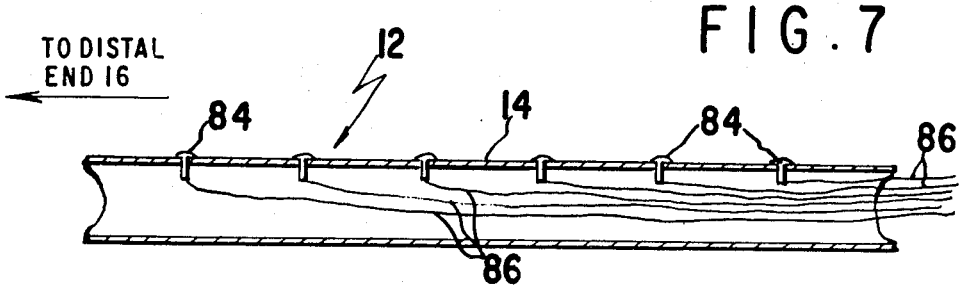
Figure 12:
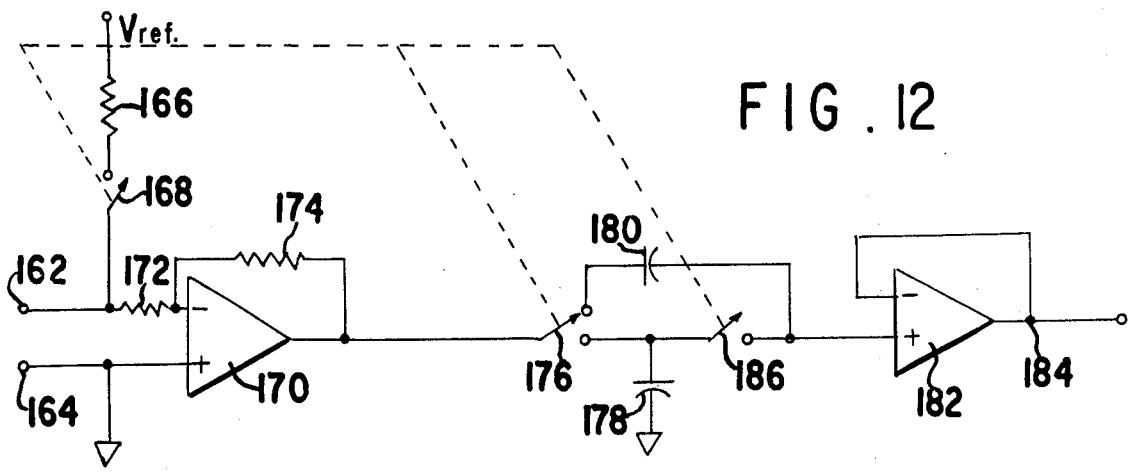
FIG. 12 is a schematic diagram of a circuit for use in the present invention.

FIG. 7 is a cross-sectional view, partially cut away, of yet another embodiment of the present invention, wherein elements corresponding to those shown in the preceding figures are identified by the same reference numerals. In the device of FIG. 7, a plurality of ECG electrodes 84 are positioned on the outer wall of the tube 14 at regularly spaced axial locations and in radial alignment with one another. Each electrode 84 has a projection extending through the tube 14 and into its lumen. A plurality of conductors 86 each have a first end connected to a respective electrode 84 and extend through the lumen of the tube 14 to its proximal end and therefrom through the tube 30 for coupling to ECG detecting means. As in the case of the above described embodiments, the tube 34 (not shown in FIG. 7) is disposed in side by side relationship with the tube 14 and displaced radially by 90 degrees from the electrodes 84, for maintaining the electrodes 84 in contact with the cervical wall. Accordingly, those electrodes which are in contact with the cervical wall will detect the maternal ECG signal thus providing a means of detecting the position of the cervical wall with respect to the axial dimension of tube 14, thus to provide a means for monitoring the recession of the cervical wall with the progression of labor.

With reference now to FIGS. 8 through 15, yet another embodiment of the present invention is illustrated. FIG. 8 is a plan view of a distal portion of a device 100 for use in monitoring several different physiological parameters during labor, namely, cervical dilatation, intrauterine pressure, maternal ECG, and cervical capillary blood flow. Device 100 includes a first tube 102 for use in measuring intrauterine pressure and a second tube 104 in side by side relationship with tube 102 to serve as a conduit for wires connected to sensors described herein below. Device 100 also includes a cover 106 of compressible material, such as latex rubber, over its distal portion and extending from a proximal end 110 to a sealed distal end 108. 100 also includes elongated dilatation monitoring device 111 extending axially with tubes 102 and 104 from a proximal end 113 of device 111 to a distal end 115 of device 111 positioned several centimeters axially from the distal ends of tubes 102 and 104.

With reference also to FIGS. 9 and 11, a sponge 114 is positioned within cover 106. Sponge 114 has a recess 117 covering the distal ends of tubes 102 and 104 and extending proximally several centimeters therefrom. The sponge 114 also extends from the distal ends of tubes 102 and 104 to distal end 108 of cover 106. Cover 106 has a plurality of pinholes 116 therethrough adjacent its distal end 108 and tube 102 also has a plurality of pinholes 118 therethrough adjacent its distal end. The device 100 is sized to be positioned between a cervical wall and a fetal presenting part in the lower uterine segment during labor. When device 100 is thus positioned, pinholes 116 permit uterine fluids to pass through cover 106 and be absorbed by spong 114. A portion of the fluid passes through pinholes 116 and enters the lumen of tube 102 through pinholes 118. The lumen of tube 102 is sized to permit the conduction of the fluids therethrough by capillary action. The proximal end of tube 102 is adapted to be coupled to a strain gauge, as described below, to permit the monitoring of uterine pressure during labor.

Conventional uterine pressure catheters are prone to become clogged at their uterine apertures due to the clotting of blood in these apertures. Sponge 114 of device 100, having been filled with uterine fluid, will eject the fluid when compressed through cover 106 as contractions occur. Accordingly, the uterine fluid about pinholes 116 is thus agitated which deters the formation of blood clots in pinholes 116, which thus aids in maintaining their patency.

With reference to FIGS. 8 and 11, device 100 also includes a capillary blood flow sensor 120 such as that disclosed in my U.S. patent application entitled "Monitoring of Capillary Blood Flow" filed concurrently herewith. Sensor 120 has a generally cylindrical base 122 mounted on the sponge adjacent its proximal end, the base 122 projecting through an aperture in cover 106. A surface of base 122 outside the cover 106 has a plurality of infrared radiation transmitters 124 and a photoresponsive element 126 projecting outwardly of the surface for contacting the cervical wall. Wires for coupling the transmitters 124 and element 126 to monitoring apparatus extend outwardly of base 122 and enter tube 104 via an aperture therein (not shown) and extend through the proximal end thereof for coupling to monitoring apparatus, as described hereinbelow. As the sponge 114 absorbs uterine fluid, it expands to press the sensor 120 into the cervical wall. At the same time, sponge 114 is yieldable beneath sensor 120 to avoid excessive pressure against the cervical wall.

With reference to FIGS. 8, 10 and 11, device 100 also includes an elongated device 111 for use in monitoring cervical dilatation during labor. Device 111 is disposed to extend longitudinally in side-byside relationship with tubes 102 and 104 from a proximal end 113 positioned axially several millimeters proximally of end 110 of cover 106, therefrom beneath cover 106 to a distal end 115 of device 111 adjacent the proximal end of sponge 114. As an alternative to the arrangement shown in FIGS. 8–11, the device 111 may be positioned between tubes 102 and 104, so that the latter are split radially thereat. Device 111 includes an elongated base 130 of compressible material, such as latex rubber, and having a central lumen extending axially thereof. Device 111 also includes an elongated resistive element 132 comprising an elongated central support 134 having a generally flattened cross-section (as seen in FIG. 10) and a resistive wire 136 wound helically thereabout. Element 132 extends axially within the central lumen of base 130. An electrically conductive, elongated element 138 also extends axially within the central lumen of base 130. Element 138 includes a central cylindrical support 140 and a conductive wire 142 wound helically about support 140. With reference to FIG. 11, wire 142 at the distal end of element 138 is connected electrically with resistive wire 136 at its distal end.

With reference to FIGS. 10 and 11, conductive element 138 is spaced from contact with resistive element 132 by two inwardly facing projections 144 of base 130. Projections 144 define an axially extending aperture therebetween. Since both cover 106 and base 130 are made of compressible material, those portions of the device 100 disposed between the cervical wall and the fetal presenting part will be compressed to force the axially corresponding portions of elements 132 and 138 together. Accordingly, as the cervical wall recedes along the device 100 with dilatation, this may be monitored in time continuous fashion by monitoring the resistance between elements 132 and 138. This is facilitated by connecting two wires 150 and 152 each to a proximal end of a respective one of elements 132 and 138, and leading such wires into tube 104 through an aperture 154 therein and through the lumen of tube 104 to its proximal end for coupling to monitoring apparatus, as described hereinbelow.

A portion 160 of conductive element 138 is directed through base 130 and cover 106 for contacting the cervical wall to detect the maternal ECG therefrom. A circuit useful for producing either a signal proportional to the maternal ECG or a signal proportional to the resistance between elements 132 and 138 is illustrated schematically in FIG. 12. Two input terminals 162 and 164 are provided for coupling the FIG. 12 circuit respectively to elements 138 and 132. A first resistor 166 has one terminal connected to a source of constant voltage $V_{ref}$ and a second terminal connected to a first terminal of an SPST switch 168. A second terminal of switch 168 is connected to terminal 162.

A first operational amplifier 170 has an inverting input terminal connected to a first terminal of an input resistor 172. A second terminal of resistor 172 is connected to terminal 162. Amplifier 170 has a non-inverting input terminal connected to terminal 164 and to equipment ground. A feedback resistor 174 is connected between an output terminal of amplifier 170 and its inverting input terminal.

The output terminal of amplifier 170 is connected to the moveable terminal of a SPDT switch 176. A first fixed terminal of switch 176 is coupled to a first terminal of a capacitor 178 having a second terminal connected to equipment ground. A second fixed terminal of switch 176 is connected to a first terminal of a capacitor 180 having a second terminal connected to the non-inverting input of a second operational amplifier 182 connected in a voltage follower configuration.

Amplifier 182 has an output terminal 184. A second SPST switch 186 has a first terminal connected to the first terminal of capacitor 178 and a second terminal connected to the non-inverting input of amplifier 182.

Switches 168, 176 and 186 are ganged for operation as follows. When it is desired to measure cervical dilatation, switch 168 is closed to couple the second terminal of resistor 166 to terminal 162 and, simultaneously, the moveable terminal of switch 176 is coupled to capacitor 178 (to ground the maternal ECG signal) and the first fixed terminal of switch 186 is connected to its second fixed terminal. When it is desired to monitor maternal ECG, the switches are reversed in polarity to disconnect $V_{ref}$ and AC couple the maternal ECG signal from the output of amplifier 170 to the non-inverting input of amplifier 182. The maternal ECG signal may be detected for use in diagnosing fetal death, as disclosed in my U.S. patent application entitled "Detection of Fetal Death" filed concurrently herewith.

Figure 13:
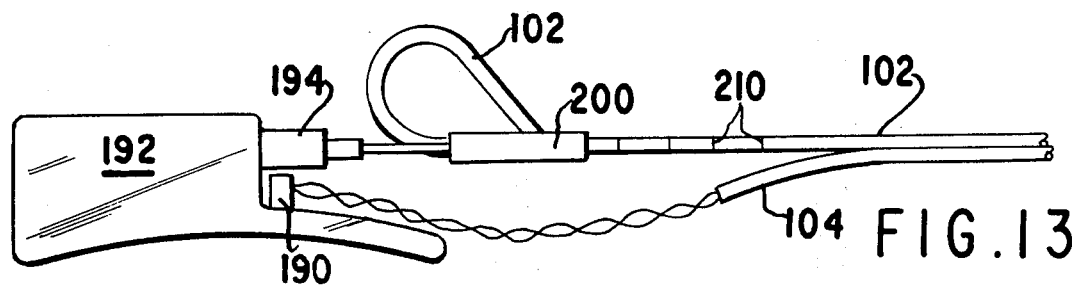
FIG. 13 illustrates a leg plate for use in coupling signals from a device of FIGS. 8-12 to monitoring apparatus, as well as for transducing pressure in a fluid filled tube of the device to an electrical signal.
Figure 14:
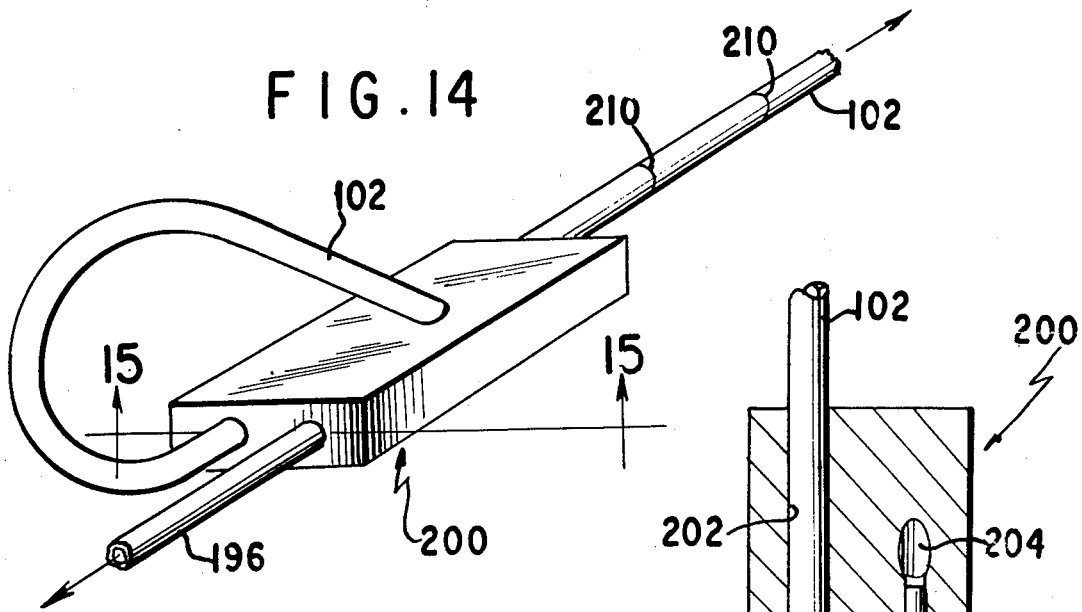
FIG. 14 is a perspective view of a collar designed to coact with the device of FIGS. 8-12 for monitoring fetal descent.

FIG. 13 illustrates a leg plate useful for coupling signals from the device 100 to monitoring apparatus as well as for transducing pressure in the fluid filled tube 102 to an electrical signal. The wires from sensor 120 as well as from device 111 pass outwardly of the proximal end of tube 104 and are coupled to respective input terminals (represented by the input terminal 190) mounted on a base 192 of the leg plate. A tocotransducer (not shown) is mounted in base 192 and is provided with a coupling 194 projecting from base 192. Coupling 194 in turn is coupled to a luer-type connector 196 at one end thereof. A second end of connector 196 is inserted into a first bore 206 of a collar 200, illustrated in greater detail in FIGS. 14 and 15.

Figure 15:
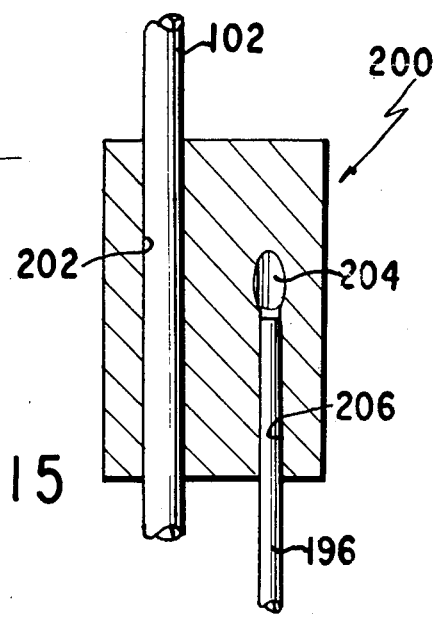
FIG. 15 is a partially cross sectional view taken along the lines 15—15 in FIG. 14.

Collar 200 is designed to coact with tube 102 for monitoring fetal descent. With reference first to FIG. 15, collar 200 has a second bore 202 through which tube 102 passes. Collar 200 is made of a material such as Teflon or other low-friction type material to permit tube 102 to slide freely through bore 202. As tube 102 exits bore 202 at its proximal end, it is curved back toward collar 200 approximately 225° and enters a third bore 204 in collar 200 at about 45° to the surface thereof. Third bore 204 intersects first bore 206 so that connector 196 is in fluid communication with tube 102 which, therefore, is in fluid communication with coupling 194 so that the pressure in tube 102 may be transduced to a pressure signal by the tocotransducer.

In order to monitor fetal descent, a plurality of markings 210 are provided on tube 102 and spaced axially therealong at intervals of 1 centimeter. The distal end of device 100 is provided with means for affixing to the fetal presenting part. For example, a plurality of suction cups may be provided on the side of cover 106 which contacts the fetal presenting part. In the alternative, a sparingly soluble, sticky substance, such as molasses may be spread on this side of cover 106 which is then pressed against the fetal presenting part to be affixed thereto. As the fetus descends, the tube 102, therefore, is pushed proximally and slides through the bore 202, since the collar is anchored with respect to the maternal leg as a reference, by the leg plate. The clinician is thus able to monitor fetal descent by observing the position of the markings 210 with respect to collar 200.

Having described certain preferred embodiments of the invention with reference to the accompanying drawings, it is to be understood that the present invention is not limited to these precise embodiments and that various changes and modifications therein can be effected by one skilled in the art without departing from the spirit and scope of the invention as defined in the appended claims.

I claim:

1. A device for use in monitoring cervical dilatation during labor comprising:
    an elongated flexible compressible member having a longitudinal axis and being adapted for positioning between a fetal presenting part and a cervix; and
    means for measuring the recession of the cervix along the longitudinal axis of the elongated compressible member during cervical dilatation which include pressure detecting means having a plurality of pressure responsive switches spaced axially along the member for detecting a position along the longitudinal axis of the member at which pressure is exerted thereon by the fetal presenting part and the cervix.

2. The device of claim 1, wherein the elongated member is a tube.

3. The device of claim 2 further comprising electrode means for receiving a maternal ECG signal from the cervix, and wherein each of the switches comprises projection means and pad means for coupling a maternal ECG signal to means for detecting the maternal ECG signal, and wherein each switch is responsive to compression of the tube at said switch to connect the projection means to the pad means.

4. The device of claim 3 wherein the electrode means comprise a plurality of electrodes spaced axially along an outer wall of and radially aligned relative to the tube, and wherein the projection means comprises a plurality of projections, each electrode being aligned relative to the axial direction of the tube with and connected to a respective one of the projections.

5. The device of claim 3 or 4 further comprising means for positioning the electrode means to contact the cervix.

6. The device of claim 5, wherein the positioning means comprises a second tube affixed to the elongated tube in side-by-side relationship therewith.

7. The device of claim 5 wherein the positioning means comprises a second tube affixed to the elongated tube in side-by-side relationship therewith for use in measuring intrauterine pressure.

8. The device of claim 2 wherein each of the plurality of pressure responsive switches comprises a first switch contact mounted on an interior wall of the tube and a second switch contact mounted on the interior wall opposite said first switch contact.

9. A method of monitoring cervical dilatation during labor comprising the steps of:
    positioning an elongated member having a longitudinal axis between a fetal presenting part and a cervix; and
    measuring the recession of the cervix during cervical dilatation along the longitudinal axis of the elongated member by detecting a maternal ECG signal at at least one locus of contact between the elongated member and the cervix.

* * * * *